United States Patent [19]

Yamaguchi et al.

[11] Patent Number: 5,274,166

[45] Date of Patent: Dec. 28, 1993

[54] DITHIOCARBAMIC ACID SALT, PROCESS FOR PRODUCTION THEREOF, AND PROCESS FOR PRODUCTION OF ISOTHIOCYANATE USING SAID DITHIOCARBAMIC ACID SALT

[75] Inventors: Mikio Yamaguchi; Hideo Ohi, both of Shizuoka, Japan

[73] Assignee: Ihara Chemical Industry Co., Ltd., Tokyo, Japan

[21] Appl. No.: 930,435

[22] PCT Filed: Jan. 29, 1992

[86] PCT No.: PCT/JP92/00082

§ 371 Date: Sep. 30, 1992

§ 102(e) Date: Sep. 30, 1992

[87] PCT Pub. No.: WO92/13835

PCT Pub. Date: Aug. 20, 1992

[30] Foreign Application Priority Data

Jan. 30, 1991 [JP] Japan .................. 3-32001

[51] Int. Cl.$^5$ .................................. C07F 9/38
[52] U.S. Cl. ................... 560/17; 558/235; 558/236; 544/351; 546/283; 562/27
[58] Field of Search ........... 560/17; 568/20; 558/235, 236; 562/27; 544/351; 546/283

[56] References Cited

U.S. PATENT DOCUMENTS 3,923,854 12/1975 Duerr .................. 558/235
5,039,331 8/1991 Satow .................. 544/235

FOREIGN PATENT DOCUMENTS 0750053 11/1970 Belgium .
63-33358 2/1988 Japan .
1-250388 10/1989 Japan .
2-188588 7/1990 Japan .
2-193961 7/1990 Japan .

*Primary Examiner*—Jose' G. Dees
*Assistant Examiner*—Samuel Barts
*Attorney, Agent, or Firm*—Oblon, Spivak, McClelland, Maier & Neustadt

[57] ABSTRACT

The present invention provides a dithiocarbamic acid salt which can be converted, at a very high yield, to an isothiocyanate suitable for use as an intermediate for production of thiazabicyclononane derivative or monothiourazole derivative; a process for producing said dithiocarbamic acid salt at a high yield without using thiophosgene having a toxicity problem; and a process for producing an isothiocyanate using said dithiocarbamic acid salt.

The dithiocarbamic acid salt of the present invention is represented by general formula (2), and the process for producing said dithiocarbamic acid salt (2) comprises reacting an aniline represented by general formula (5) with carbon disulfide in the presence of 1,4-diazabicyclo[2.2.2]octane (3) or 4-pyrrolidinopyridine (4).

The process for producing an isothiocyanate (1) according to the present invention comprises reacting the above dithiocarbamic acid salt (2) with a halogen compound.

4 Claims, No Drawings

DITHIOCARBAMIC ACID SALT, PROCESS FOR PRODUCTION THEREOF, AND PROCESS FOR PRODUCTION OF ISOTHIOCYANATE USING SAID DITHIOCARBAMIC ACID SALT

TECHNICAL FIELD

The present invention relates to a dithiocarbamic acid salt suitable for use as an intermediate for production of thiazabicyclononane derivative or monothiourazole derivative (these derivatives are each useful as an agricultural chemical, for example, a herbicide); a process for production thereof; and a process for producing an isothiocyanate also suitable for use as said intermediate.

BACKGROUND ART

Recently, an attention has been paid to isothiocyanates having a substituent at the 5-position, for example, an isothiocyanate represented by the following formula,

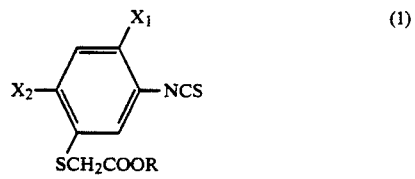

, wherein $X_1$ and $X_2$ each represent a halogen atom and R represents an alkyl group, as an intermediates used for production of thiazabicyclononane derivative or monothiourazole derivative. Such an isothiocyanate has conventionally been produced by a process represented by, for example, the following reaction formula.

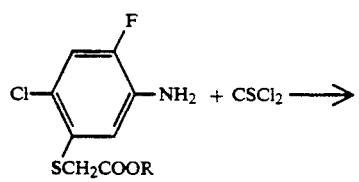

This process gives an excellent yield but has had problems in that the thiophosgene $CSCl_2$ used is difficult to procure because of its high toxicity and transportation problem, making it difficult to carry out the process industrially.

For the conversion of aniline to isothiocyanate as aimed at in the above conventional process, there are known, for example, a process represented by the following reaction formula,

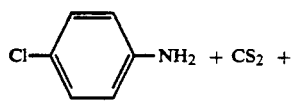

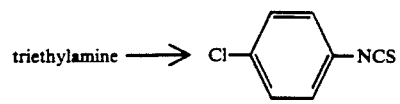

which is described in "Shin Jikkenkagaku Koza 14 (phonetical translation), Syntheses and Reactions of Organic Compounds III", pp. 1504–1505, compiled by the Chemical Society of Japan and published by Maruzen Co., Ltd. on Feb. 20, 1978, and a process using a special base, i.e. 1,8-diazabicyclo[5.4.0]-undec-7-ene (DBU), represented by the following reaction formula

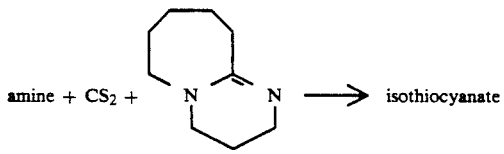

(in this process, the amine is an aliphatic amine, an alicyclic amine or an aromatic amine), which is described in Japanese Patent Application Kokai (Laid-Open) No. 33359/1988. Hence, it is considered to use these processes in producing the isothiocyanate represented by the above formula (1).

However, when the conventional process described in "Shin Jikkenkagaku Koza 14" is applied for producing an intended isothiocyanate from an aniline having a substituent at the 5-position, no reaction proceeds. And when the conventional process described in Japanese Patent Application Kokai (Laid-Open) No. 33359/1988 is applied for producing an intended isothiocyanate, the yield is as low as about 35% and the resulting isothiocyanate is converted to an ultimate product via further several steps; thus, this process is not suitable, either, for industrial application.

The present invention has been made in order to solve the above-mentioned problems of the prior art and provide a dithiocarbamic acid salt which can be converted, at a very high yield, to an isothiocyanate suitable for use as an intermediate for production of thiazabicyclononane derivative or monothiourazole derivative, and a process capable of producing said dithiocarbamic acid salt at a high yield without using any compound having toxicity problem.

The present invention has also been made in order to provide a process for producing the above isothiocyanate using said dithiocarbamic acid salt.

DISCLOSURE OF THE INVENTION

The dithiocarbamic acid salt of the present invention adopted in order to achieve the above object, is characterized by being represented by the following general formula

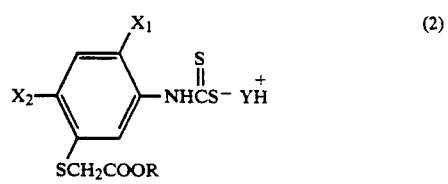

wherein $X_1$ and $X_2$ each represent a halogen atom; R represents an alkyl group; and Y represents an amine represented by the following formula

 (3)

or

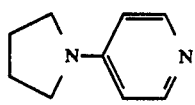 (4)

The process for producing the dithiocarbamic acid salt is characterized by reacting an aniline represented by the following general formula

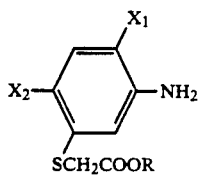 (5)

wherein $X_1$ and $X_2$ each represent a halogen atom and R represents an alkyl group, with carbon disulfide in the presence of an amine represented by the following formula

 (3)

or

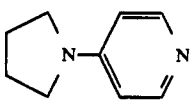 (4)

Further, the process for producing an isothiocyanate according to the present invention adopted in order to achieve the above object, is characterized by reacting a dithiocarbamic acid salt represented by the following general formula

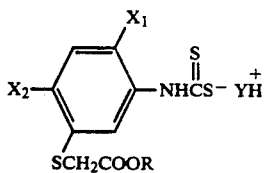 (2)

wherein $X_1$ and $X_2$ each represent a halogen atom; R represents an alkyl group; and Y represents an amine represented by the following formula

 (3)

-continued
or

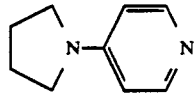 (4)

, with a halogen compound.

The present inventors made a study on the reaction conditions to convert an aniline (5) having a substituent at the 5-position to an isothiocyanate (1) and, as a result, found that a dithiocarbamic acid salt (2) can be obtained at a high yield by using a base, i.e. an amine represented by the above formula (3) or (4) and that this dithiocarbamic acid salt can be converted easily and at a very high yield to an intended isothiocyanate (1). The present invention has been completed based on the above finding.

BEST MODE FOR CARRYING OUT THE INVENTION

The present invention is hereinafter described in detail.

The solvent usable in the present process for producing a dithiocarbamic acid salt, can be exemplified by hydrocarbons such as benzene, toluene, cyclohexane, n-hexane and the like; halogenated hydrocarbons such as chloroform, ethylene chloride, dichloromethane, dichlorobenzene, chlorobenzene, trichloroethane, tetrachloroethane, o-, m- or p-chlorotoluene and the like; ethers such as ethyl ether and the like; and water. However, the solvent is not particularly restricted in the present process for producing a dithiocarbamic acid salt.

As the amine usable in the present production process, there can be mentioned 1,4-diazabicyclo[2.2.2]octane represented by the following formula

 (3)

or 4-pyrrolidinopyridine represented by the following formula

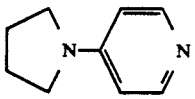 (4)

As the reaction temperature, there can be mentioned, for example, a range of 100° C. or below, preferably −40° C. to 40° C.; and as the molar ratio of the compounds used in the reaction, there can be mentioned, for example, a range of aniline:carbon disulfide:amine=1-:1-30:1-30. In the present process for producing a dithiocarbamic acid salt, however, the molar ratio of the compounds used in the reaction need not be strictly specified.

As the reaction time, there can be mentioned, for example, a range of 1-500 hours, preferably 5-30 hours.

With respect to the procedure adopted in the above reaction, an aniline, carbon disulfide and an amine can be reacted in a solvent such as mentioned above. In this reaction, since a dithiocarbamic acid salt appears as a precipitate, filtration is conducted to obtain it as an intended product. The amine used is recovered and can be reused.

That the dithiocarbamic acid salt of the present invention obtained by the above procedure has a structure represented by the following formula

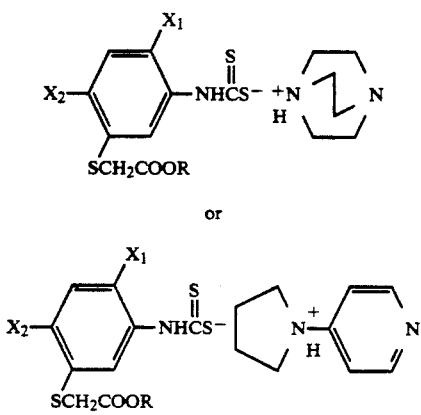

is well supported by the results of various instrumental analyses, particularly elemental analysis for said compound.

The production of isothiocyanate from the dithiocarbamic acid salt obtained as above, can be conducted by the present process for production of isothiocyanate, described below.

The present process for production of isothiocyanate comprises reacting a dithiocarbamic acid salt with a halogen compound in a solvent with stirring and then subjecting the reaction mixture to water washing, drying and concentration to obtain an intended isothiocyanate. In this reaction, as the halogen compound, there can be used halogenated carbonic acid esters such as methyl chlorocarbonate, ethyl chlorocarbonate and the like, halogenated alkyls, etc. The use of a halogenated carbonic acid ester is preferred. As the solvent, there can be used halogenated hydrocarbons such as dichloromethane, chloroform and the like; alcohols such as ethanol, methanol and the like; aromatic hydrocarbons such as benzene, toluene and the like; water; and so forth.

As the reaction temperature, there can be mentioned, for example, a range of −80° C. to 120° C., preferably −40° C. to 40° C. As the molar ratio of the compounds used in the reaction, there can be mentioned, for example, a range of dithiocarbamic acid salt:halogen compound=1:1−10, preferably 1:1−2.

As the reaction time, there can be mentioned, for example, a range of 0.5-20 hours, preferably 1-10 hours.

The structure of the isothiocyanate obtained according to the above reaction procedure can be confirmed by comparing the results of instrumental analyses for the compound, with data described in literatures, etc. In obtaining an isothiocyanate as a final product, the following steps aniline→dithiocarbamic acid salt→isothiocyanate may be conducted continuously without isolating the intermediate product.

The present invention is described by way of Examples.

EXAMPLE 1

Into a 100-ml four-necked reaction flask fitted with a thermometer, a Jimroth condenser and a dropping funnel were fed 2.4 g (10 mM) of 4-chloro-2-fluoro-5-methoxy-carbonyl-methylthioaniline, 3.36 g (30 mM) of 1,4-diazabicyclo[2.2.2]-octane and 16 ml of toluene. Thereto was dropwise added 2.28 g (30 mM) of carbon disulfide from the dropping funnel at room temperature. After the dropwise addition, the mixture was stirred at room temperature for 20 hours to complete a reaction. After the completion of the reaction, the precipitated crystals were collected by filtration to obtain 4.28 g of 1,4-diazabicyclo[2.2.2]octanium-N-(4-chloro-2-fluoro-5-methoxycarbonylmethylthiophenyl)dithiocarbamate. The yield was 98%. The properties of the compound are shown below.

| Melting point: 138-139° C. | | | |
|---|---|---|---|
| Elemental analysis: | H | C | N |
| Calculated | 4.83 | 43.88 | 9.59 |
| Obtained | 4.69 | 43.40 | 9.70 |
| Infrared absorption spectrum (cm$^{-1}$): | 2855, 1740, 1465, 1295, 1005, 600 | | |

Example 2

Into a 100-ml reaction flask fitted with a thermometer, a Jimroth condenser and a dropping funnel were fed 4.28 g (9.8 mM) of the dithiocarbamate obtained in Example 1 and 50 ml of dichloromethane. A mixed solution consisting of 1.01 g(10.7 mM) of methyl chlorocarbonate and 3 ml of dichloromethane were dropwise added slowly from the dropping funnel at 0° C. with cooling. After the dropwise addition, stirring was conducted at 0° C. for an additional 5 hours to complete a reaction. The reaction mixture was water-washed, dried over magnesium sulfate and concentrated to remove dichloromethane to obtain 2.70 g of 4-chloro-2-fluoro-5-methoxycarbonylmethylthiophenyl isothiocyanate. The yield was 95%. The melting point of the compound was 68°-70° C.

COMPARATIVE EXAMPLE 1

A reaction was conducted in the same procedure as in Example 1 except that triethylamine (30 mM) was used in place of 1,4-diazabicyclo[2.2.2]octane (30 mM). As a result, there was obtained no triethylammonium-N-(4-chloro-2-fluoro-5-methoxycarbonylmethylthiophenyl)-dithiocarbamate.

COMPARATIVE EXAMPLE 2

A reaction was conducted in the same procedure as in Example 1 except that 1,8-diazabicyclo[5.4.0]undec-7-ene (30 mM) was used in place of 1,4-diazabicyclo[2.2.2]octane (30 mM). As a result, there was obtained 5.0 g of 1,8-diazaabicyclo[5.4.0]undecene-7-enium-N-(4-chloro-2-fluoro-5-methoxycarbonylmethylthiophenyl)dithiocarbamate. The yield was 35%. In this reaction, large amounts of by-products were formed.

Example 3

A reaction was conducted in the same procedure as in Example 1 except that 4.45 g (30 mM) of 4-pyrrolidinopyridine was used in place of 3.36 g (30 mM) of 1,4-diazabicyclo-[2.2.2]octane. As a result, there was obtained 4.54 g of 4-pyrrolidinopyridinium-N-(4-chloro-2-fluoro-5-methoxycarbonyl-methylthiophenyl)dithiocarbamate. The yield was 96%. The properties of the compound are shown below.

| | |
|---|---|
| Melting point: | 92-93.5° C. |
| Infrared absorption spectrum (cm$^{-1}$): | 1570, 1255, 1200 |
| $^1$H-NMR (DMSO d-6, δ): | 1.6-2.2, 3.0-3.7 (Pyro, m, 8H), 3.6 (CH$_3$, s, 3H), 3.8 (CH$_2$, s, 2H), 6.6, 8.2 (Py, abq, Jab = 0.8 Hz), 7.2, 7.6 (aro, s, 2H), 9.9 (NH, bs, 2H) |

EXAMPLE 4

Into a 100-ml reaction flask fitted with a thermometer, a Jimroth condenser and a dropping funnel were fed 4.54 g (9.6 mM) of the dithiocarbamate obtained in Example 3 and 50 ml of dichloromethane. A mixed solution consisting of 1.01 g (10.7 mM) of methyl chlorocarbonate and 3 ml of dichloromethane were dropwise added slowly from the dropping funnel at 0° C. with cooling. After the dropwise addition, stirring was conducted at 0° C. for an additional 5 hours to complete a reaction. The reaction mixture was water-washed, dried over magnesium sulfate, and concentrated to remove dichloromethane to obtain 2.63 g of 4-chloro-2-fluoro-5-methoxycarbonylmethylthiophenyl isothiocyanate. The yield was 94%. The compound had a melting point of 68°-70° C.

INDUSTRIAL APPLICABILITY

The aniline used as a starting material in the present invention, when reacted with carbon disulfide and an ordinary base, gives no intended isothiocyanate, or gives it at a low yield with by-products being formed in some cases. In the present invention, however, an intended isothiocyanate can be obtained at a high yield (93%) by using, as a base, an amine such as mentioned above.

When said amine is used as in the present invention, an intended dithiocarbamic acid salt is precipitated from the reaction system and therefore easy to isolate by filtration, etc.

Further in the present invention, an isothiocyanate can be produced at a high yield without using thiophosgene, and the recovery and reuse of said amine is easy. Thus, the present invention is particularly effective when an aniline having a substituent at the 5-position is used as a starting material.

We claim:

1. A dithiocarbamic acid salt characterized by being represented by the following formula

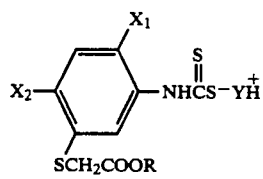

wherein X$_1$ and X$_2$ represent a halogen atom; R represents an alkyl group; and Y represents an amine represented by

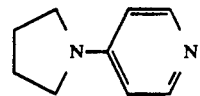

2. A dithiocarbamic acid salt according to claim 1, characterized by being represented by the following formula

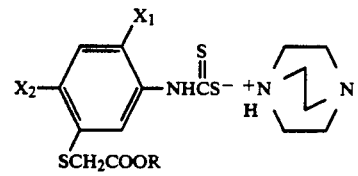

wherein X$_1$ and X$_2$ each represent a halogen atom and R represents an alkyl group.

3. A dithiocarbamic acid salt according to claim 1, characterized by being represented by the following formula

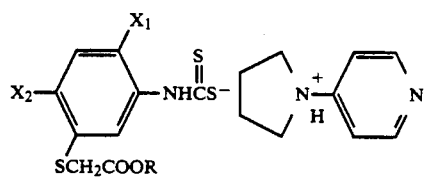

wherein X$_1$ and X$_2$ each represent a halogen atom and R represents an alkyl group.

4. A process for producing a dithiocarbamic acid salt represented by the following formula

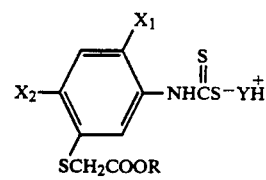

wherein X$_1$ and X$_2$ each represent a halogen atom; R represents an alkyl group; and Y represents an amine represented by

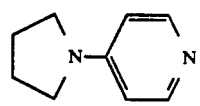

, which process is characterized by reacting an aniline represented by the following formula

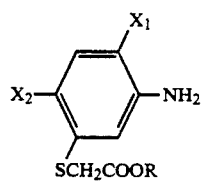
wherein $X_1$ and $X_2$ represent a halogen atom and R represents an alkyl group, with carbon disulfide in the presence of an amine represented by
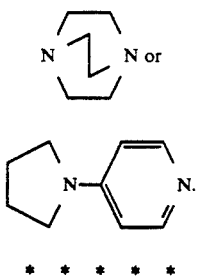
* * * * *